(12) United States Patent
Bornstein

(10) Patent No.: US 10,702,706 B2
(45) Date of Patent: Jul. 7, 2020

(54) APPARATUS, SYSTEM, AND METHOD FOR GENERATING PHOTO-BIOLOGIC MINIMUM BIOFILM INHIBITORY CONCENTRATION OF INFRARED LIGHT

(71) Applicant: NOMIR MEDICAL TECHNOLOGIES, INC., Woodmere, NY (US)

(72) Inventor: Eric Bornstein, Woodmere, NY (US)

(73) Assignee: NOMIR MEDICAL TECHNOLOGIES, INC., Woodmere, NY (US)

(*) Notice: Subject to any disclaimer, the term of this patent is extended or adjusted under 35 U.S.C. 154(b) by 0 days.

(21) Appl. No.: 14/333,066

(22) Filed: Jul. 16, 2014

(65) Prior Publication Data

US 2015/0025439 A1    Jan. 22, 2015

Related U.S. Application Data

(60) Provisional application No. 61/846,919, filed on Jul. 16, 2013.

(51) Int. Cl.
| | | |
|---|---|---|
| A61N 5/06 | (2006.01) | |
| A61K 31/351 | (2006.01) | |
| A61K 31/496 | (2006.01) | |

(52) U.S. Cl.
CPC .......... *A61N 5/0624* (2013.01); *A61K 31/351* (2013.01); *A61K 31/496* (2013.01); *A61N 2005/0659* (2013.01)

(58) Field of Classification Search
CPC ...... A61N 2005/0659; A61N 2005/063; A61B 5/0086; A61M 2205/052

(Continued)

(56) References Cited

U.S. PATENT DOCUMENTS

| | | | |
|---|---|---|---|
| 7,241,613 B1 * | 7/2007 | Willins | A61K 36/06 424/184.1 |
| 7,255,560 B2 | 8/2007 | Bornstein et al. | |

(Continued)

FOREIGN PATENT DOCUMENTS

| | | |
|---|---|---|
| WO | 2005034790 A2 | 4/2005 |
| WO | 2005055851 A2 | 6/2005 |

(Continued)

OTHER PUBLICATIONS

Krespi, et al. "Laser-assisted nasal decolonization of *Staphylococcus aureus*, including methicillin-resistant *Staphylococcus aureus*." Jan. 12, 2012. American Journal of Otolaryngology, vol. 33, pp. 572-575.*

(Continued)

*Primary Examiner* — Rebecca E Eisenberg
*Assistant Examiner* — Weng Lee
(74) *Attorney, Agent, or Firm* — The Marbury Law Group, PLLC

(57) ABSTRACT

Systems and methods are disclosed herein for prophylactic application of near-infrared optical energies and dosimetries to photo-biologically inhibit accelerations or intensifications in biofilm production, after a bacterial or fungal pathogen is challenged with an antibiotic or antifungal agent. This photo-biologic minimum biofilm inhibitory concentration (PMBIC) of infrared light will lower the minimum inhibitory concentration (MIC) necessary of an antibiotic and/or antifungal molecule necessary to decrease bacterial and fungal pathogens in human tissues. These systems and methods will only target undesirable microbial cells.

4 Claims, 13 Drawing Sheets

(58) Field of Classification Search
USPC ............................... 604/20, 21; 607/88–93
See application file for complete search history.

(56) References Cited

U.S. PATENT DOCUMENTS

| | | | |
|---|---|---|---|
| 7,470,124 | B2 | 12/2008 | Bornstein |
| 7,621,745 | B2 | 11/2009 | Bornstein |
| 7,713,294 | B2 | 5/2010 | Bornstein et al. |
| 8,430,919 | B2 | 4/2013 | Bornstein |
| 8,506,979 | B2 | 8/2013 | Bornstein |
| 8,535,359 | B2 | 9/2013 | Bornstein |
| 2002/0004220 | A1* | 1/2002 | Dong ............... C12Q 1/18 435/32 |
| 2003/0125783 | A1* | 7/2003 | Moran ............ A61N 5/0616 607/89 |
| 2004/0126272 | A1 | 7/2004 | Bornstein |
| 2004/0156743 | A1 | 8/2004 | Bornstein |
| 2007/0197884 | A1 | 8/2007 | Bornstein |
| 2008/0008980 | A1 | 1/2008 | Bornstein |
| 2008/0021370 | A1 | 1/2008 | Bornstein |
| 2008/0077204 | A1 | 3/2008 | Bornstein |
| 2008/0131968 | A1 | 6/2008 | Bornstein |
| 2008/0138772 | A1 | 6/2008 | Bornstein |
| 2008/0159345 | A1 | 7/2008 | Bornstein |
| 2008/0267814 | A1 | 10/2008 | Bornstein |
| 2009/0087816 | A1 | 4/2009 | Bornstein |
| 2009/0118721 | A1* | 5/2009 | Bornstein .................. 606/13 |
| 2009/0299263 | A1 | 12/2009 | Bornstein |
| 2011/0070552 | A1 | 3/2011 | Bornstein |
| 2011/0082525 | A1 | 4/2011 | Bornstein |
| 2011/0208274 | A1 | 8/2011 | Bornstein |
| 2011/0212411 | A1 | 9/2011 | Sinofsky |
| 2011/0295343 | A1* | 12/2011 | Bornstein ............ A61N 5/0616 607/88 |
| 2012/0156635 | A1 | 6/2012 | Bornstein |

FOREIGN PATENT DOCUMENTS

| | | |
|---|---|---|
| WO | 2005087317 A1 | 9/2005 |
| WO | 2005102033 A2 | 11/2005 |
| WO | 2007014130 A2 | 2/2007 |
| WO | 2007019305 A2 | 2/2007 |
| WO | 2007064787 A2 | 6/2007 |
| WO | 2007087374 A2 | 8/2007 |
| WO | 2008013792 A2 | 1/2008 |
| WO | 2008073979 A2 | 6/2008 |
| WO | 2009059223 A2 | 5/2009 |
| WO | 2009059230 A2 | 5/2009 |
| WO | 2009059233 A2 | 5/2009 |
| WO | 2009082547 A1 | 7/2009 |
| WO | 2009117672 A2 | 9/2009 |
| WO | 2009117675 A1 | 9/2009 |
| WO | 2010019800 A1 | 2/2010 |
| WO | 2010051463 A2 | 5/2010 |
| WO | 2010056537 A1 | 5/2010 |

OTHER PUBLICATIONS

Co-pending U.S. Appl. No. 10/648,557, filed Aug. 25, 2003.
Co-pending U.S. Appl. No. 10/659,456, filed Sep. 10, 2003.
Co-pending U.S. Appl. No. 12/275,961, filed Nov. 21, 2008.
Co-pending U.S. Appl. No. 13/058,765, filed Aug. 13, 2009.
Co-pending U.S. Appl. No. 13/246,447, filed Sep. 27, 2011.
Co-pending U.S. Appl. No. 61/597,497, filed Feb. 10, 2012.
Davis S.C., et al., "Microscopic and Physiologic Evidence for Biofilm-associated Wound Colonization in vivo," Wound Repair and Regeneration, 2008, vol. 16 (1), pp. 23-29.
Gardner S.E., et al., "The Neuropathic Diabetic Foot Ulcer Microbiome is Associated with Clinical Factors," Diabetes, 2013, vol. 62 (3), pp. 923-930.
Kaplan J.B., et al., "Low Levels of Beta-Lactam Antibiotics Induce Extracellular DNA Release and Biofilm Formation in *Staphylococcus aureus*," MBio, 2012, vol. 3 (4), e00198-12.
Ogura M., et al., "Comparative Analysis of MRSA Strains Isolated from Cases of Mupirocin Ointment Treatment in Which Eradication was Successful and in Which Eradication Failed," Journal of Infection and Chemotherapy, 2013, vol. 19 (2), pp. 196-201.
Phillips P.L., et al., "Biofilms made Easy," Wounds International, 2010, vol. 1 (3), 6 pages.
Schultz G., et al., "Biofilm Maturity Studies Indicate Sharp Debridement Opens a Time-dependent Therapeutic Window," Journal of Wound Care, 2010, vol. 19 (8), pp. 320-328.

* cited by examiner

Figure 13

APPARATUS, SYSTEM, AND METHOD FOR GENERATING PHOTO-BIOLOGIC MINIMUM BIOFILM INHIBITORY CONCENTRATION OF INFRARED LIGHT

CROSS REFERENCE TO RELATED APPLICATIONS

The present application claims the benefit of U.S. Provisional Application No. 61/846,919, filed Jul. 16, 2013, the contents of which are incorporated herein by reference in their entirety.

BACKGROUND

The majority of conventional antibiotics have been created for the treatment of planktonic bacteria. Antibiotic treatment of planktonic bacteria (not bacteria within a biofilm), has been the foremost application of microbiology research beginning with the advent of penicillin, until the modern characterization of biofilms in 1978. Clinically, the implications of biofilms are serious, as bacteria and fungi in biofilms exhibit tolerance to most clinically relevant pharmacokinetic/pharmacodynamic (PK/PD) dosing regimens of antimicrobials, in spite of susceptibility of the same pathogens as planktonic cells. Indeed, sub-minimal inhibitory concentrations of antimicrobials have been shown to induce biofilm formation, as a resistance and protection mechanism. When a bacterial or fungal cell switches to the biofilm mode of growth, it undertakes a phenotypic shift in its growth progression, with a large alteration in gene regulation. Therefore, there exists a need for methods and systems that can proactively reduce the risk of serious bacterial or fungal infections, by prophylactically inhibiting biofilm formation in microbes photo-biologically, so that after antimicrobials are given in/at a target site, without intolerable risks and/or intolerable adverse effects to human tissues where the pathogens are growing, the biofilm production is inhibited.

SUMMARY

As used herein, the term "photo-biologic minimum biofilm inhibitory concentration (PMIBC)" is defined as the lowest concentration of infrared energy for which there is a reduced increase in biofilm production, when a bacterial or fungal pathogen is subsequently exposed to an antibiotic or antifungal agent. The PMBIC will therefore lower the MIC of an antibiotic and/or antifungal molecule necessary to decrease bacterial and fungal pathogens in human tissues by inhibiting biofilm production.

The present disclosure generally relates to methods and systems for the generation of infrared optical radiation in selected energies and dosimetries that will act as the photo-biologic minimum biofilm inhibitory concentration (PMBIC) of light against accelerations or intensifications of biofilm production in microbial (e.g., bacterial and/or fungal) pathogens, and thereby lower the minimum inhibitory concentration (MIC) of antimicrobial drug necessary to decrease bacterial and fungal pathogens in human tissues.

The present disclosures directed to methods, apparatuses, and systems for inhibiting biofilm production by bacteria and fungi (i.e. reducing an increase in biofilm or reducing accelerations or intensifications of biofilm production) when a bacterial or fungal pathogen is subsequently exposed to an antimicrobial (e.g. antibiotic or antifungal) agent. The PMBIC will therefore lower the MIC of an antibiotic and/or antifungal molecule necessary to decrease bacterial and fungal pathogens in human tissues.

According to methods and systems of the present invention, near infrared optical radiation in selected energies and dosimetries (herein known as NIMELS, standing for "near infrared microbial elimination system") are used for PMBIC therapy. Other features and advantages of the present invention will be set forth in the detailed description of embodiments that follow, and in part will be apparent from the description or may be learned by practice of the invention. Such features and advantages of the invention will be realized and attained by the systems, methods and apparatus particularly pointed out in the written description and claims appended hereto.

BRIEF DESCRIPTION OF THE DRAWINGS

Aspects of the invention may more fully be understood from the following description when read together with the accompanying drawings, which are to be regarded as illustrative in nature, and not limiting. The drawings are not necessarily to scale, emphasis instead being placed on the principles of the invention.

In the drawings:

FIG. 3A is a drug only treatment. FIG. 3B is an infrared light and drug treatment. As shown, the photo-biologic minimum biofilm inhibitory concentration of infrared light will lower the maximum concentration $C_{max}$ of the antimicrobial drug necessary to decrease microbial pathogens at a treatment site, by inhibiting biofilm production.

FIG. 13 shows tables of exemplary NIMELS dosimetry used to generate the experimental results shown in FIG. 12. The upper table shows NIMELS dosimetry using two wavelengths of infrared light. The lower table shows NIMELS dosimetry using a single wavelengths of infrared light.

Figure 1:
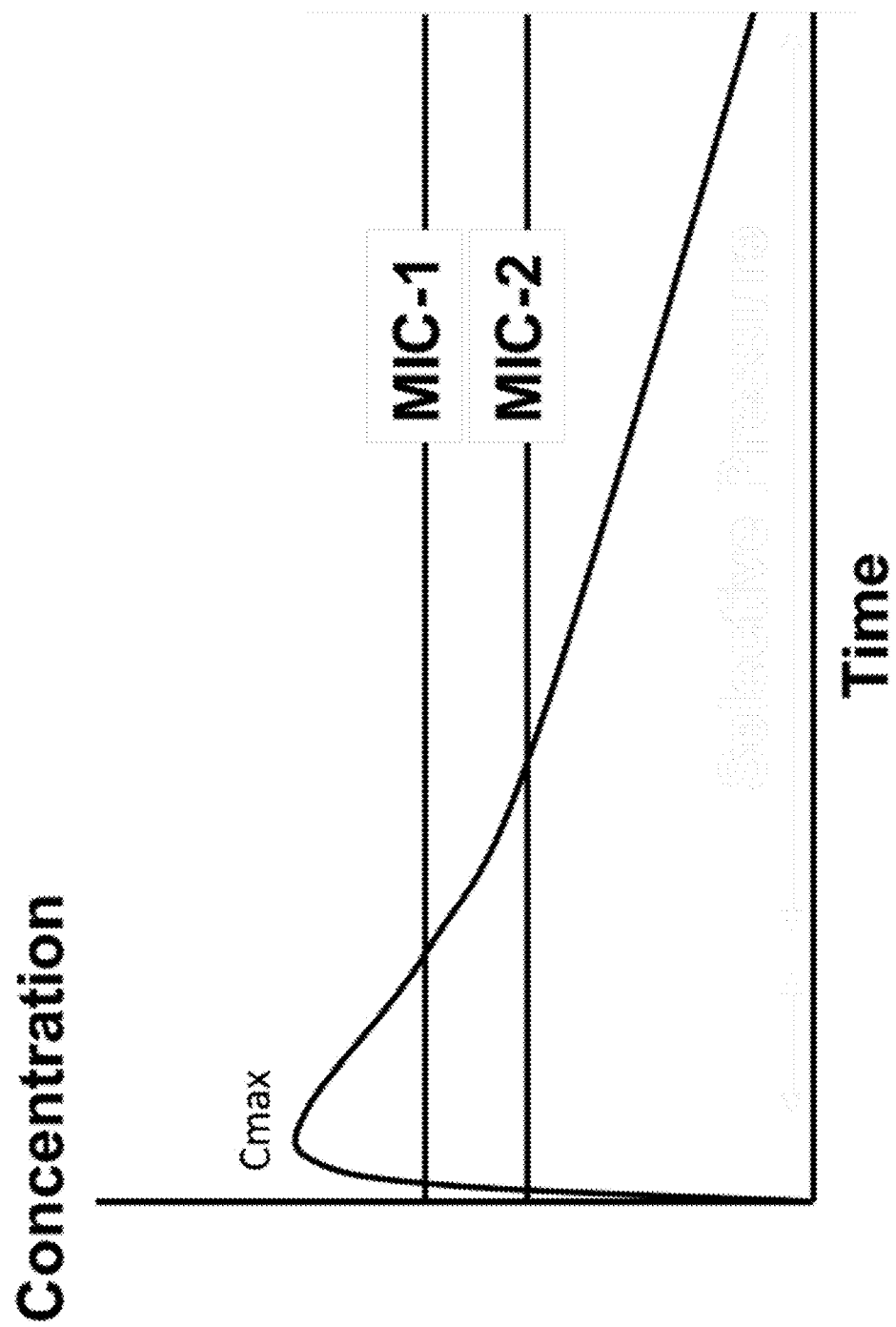
FIG. 1 is a plot of antimicrobial concentration vs. time for an exemplary treatment. MIC levels are shown before (MIC-1) and after (MIC-2) application of near infrared treatment light.

While certain embodiments depicted in the drawings and described in relation to the same, one skilled in the art will appreciate that the embodiments depicted are illustrative and that variations of those shown, as well as others described herein, may be envisioned and practiced and be within the scope of the present invention.

DETAILED DESCRIPTION

Evaluation and proper titration of antimicrobial drugs to eliminate microbes such as bacteria and fungi (to clear infections) are conventionally performed based on pharmacokinetic (PK) and pharmacodynamic (PD) measurements of the drug's action. PK measurements allow for the calculation of the half-life of antimicrobial concentrations of a drug in the body of a subject. PD measurements allow for the calculation and evaluation of the relationship between antimicrobial concentrations and their wide-ranging antimicrobial effects on the microbes. In short, pharmacokinetics with antimicrobials is simply "what the body does to the systemic drug" and pharmacodynamics with antimicrobials is "what the systemic or topical drug does to the bacteria or fungi."

For topical antimicrobial formulations, an effective therapy requires that the antimicrobial that is delivered to the site of infection be delivered in an adequate concentration to produce the desired antimicrobial effect.

Most infectious bacteria or fungi can secrete and grow inside a biofilm. This includes aerobic and anaerobic Gram-positive and Gram-negative bacteria, mycobacteria and all types of fungi. A biofilm can be initiated on foreign materials that are surgically implanted in the body (catheters, pacemakers, implants) as well as immunocompromised areas with poor blood supply such as chronic wounds. An infection caused by biofilm producing microbial organism is typically characterized by the organism's ability to enhance resistance to antimicrobials.

For example, in 2012, Kaplan et al. found that multiple different strains of methicillin resistant *Staphylococcus aureus* (MRSA) had high biofilm induction after antibiotic administration (up to a 10-fold increase). He further reported that the increased production was inversely proportional to the quantity of biofilm formed in the absence of antibiotics. Thus, antimicrobial-induced biofilm development is a very clinically relevant process, since when conventional antimicrobial dosing regimens are used, bacteria and fungi in the biofilm are continually challenged with sub-MIC concentrations of antimicrobials during the standard a course of therapy, thereby failing to resolve the infection, and possible leading to enhancement of drug resistance. This is highly problematic for conventional PK/PD dependent antimicrobial therapies that are generally based on planktonic organisms.

FIG. 1 shows a plot of antimicrobial concentration as a function of time in a subject for a typical treatment process. At early times, the antimicrobial concentration increases as the antimicrobial is applied. The concentration peaks at a maximum concentration $C_{max}$, and then decreases (e.g., as PK processes reduce the antimicrobial concentration). At long times, the antimicrobial concentration becomes negligible. In typical cases, for a portion of the treatment time, the antimicrobial concentration is higher than an MIC for a given population of pathogenic microbes. As described herein, the MIC for a given population of pathogenic microbes may be reduced by application of near-infrared treatment light having suitable wavelengths and dosimetries. As shown MIC-1 is the MIC in the absence of light treatment for a microbial population, and MIC-2 is the MIC following the application of treatment light, because of suppressed or eliminated biofilm production by the microbial organism.

Augmentation of Drug Treatment Using PMBIC

The killing of microbes is dependent on both the (a) concentration of antimicrobial drug in relation to the Minimum Inhibitory Concentration (MIC) and (b) the time that the antimicrobial MIC exposure is maintained.

Figure 2:
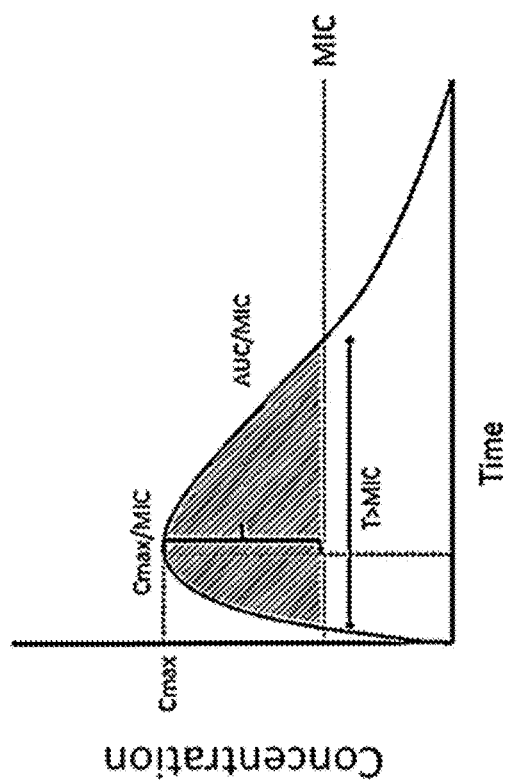
FIG. 2 is a plot of antimicrobial concentration vs. time showing various parameters for characterizing conventional concentration/time curves including (1) AUC/MIC, (2) $C_{max}$/MIC and (3) T>MIC.

FIG. 2 shows a plot of antimicrobial concentration as a function of time in a subject for a typical treatment process and annotates several key parameters for the concentration curve. When the effect of antimicrobial concentration predominates over that of time, the antimicrobial is said to be concentration-dependent and fungicidal and/or bactericidal effects are associated with an optimal maximum concentration to MIC ratio ($C_{max}$/MIC).

When the effect of antimicrobial exposure time is greater, the antimicrobial displays time-dependent activity, and antimicrobial outcomes are associated with drug concentrations above the MIC for a defined portion of the dosing interval above the MIC (T>MIC).

As can be appreciated, when antimicrobial drug treatment is used alone, enhancing treatment efficacy requires either (1) the maximum concentration of an antimicrobial and/or (2) an increased exposure time to an antimicrobial were necessary to prevent occurrence of resistant organisms. This is true, as the MIC of bacterial and fungal organisms is increasing with biofilm formation and acceleration.

Therefore, because antimicrobial therapies alone are rarely curative, especially in view of newly emergent drug resistant pathogens with augmented biofilm production, it has been imperative to develop new strategies to treat or prevent microbial infections, and especially those which inhibit microbes from producing protective biofilm.

The present disclosure describes the use of a therapeutic light source configured to generate and deliver near infrared treatment light at a target region with selected spectral properties and dosimetry. For example, as described in greater detail below, in some embodiments the near infrared treatment light delivered to the target region is substantially in a first wavelength range from about 865 nm to about 875 nm or a second radiation range having a wavelength from about 925 nm to about 935 nm, or both ranges. The dosimetry the treatment light may be controlled to treat microbial pathogens with the lowest concentration of infrared energy for which there will be a reduced increase in biofilm production, when the pathogen is subsequently exposed to an antibiotic or antifungal agent. This will lower the MIC of the infectious organisms, prior to, or concurrently with antimicrobial treatment, without damaging the tissues or area being treated.

Figure 3:
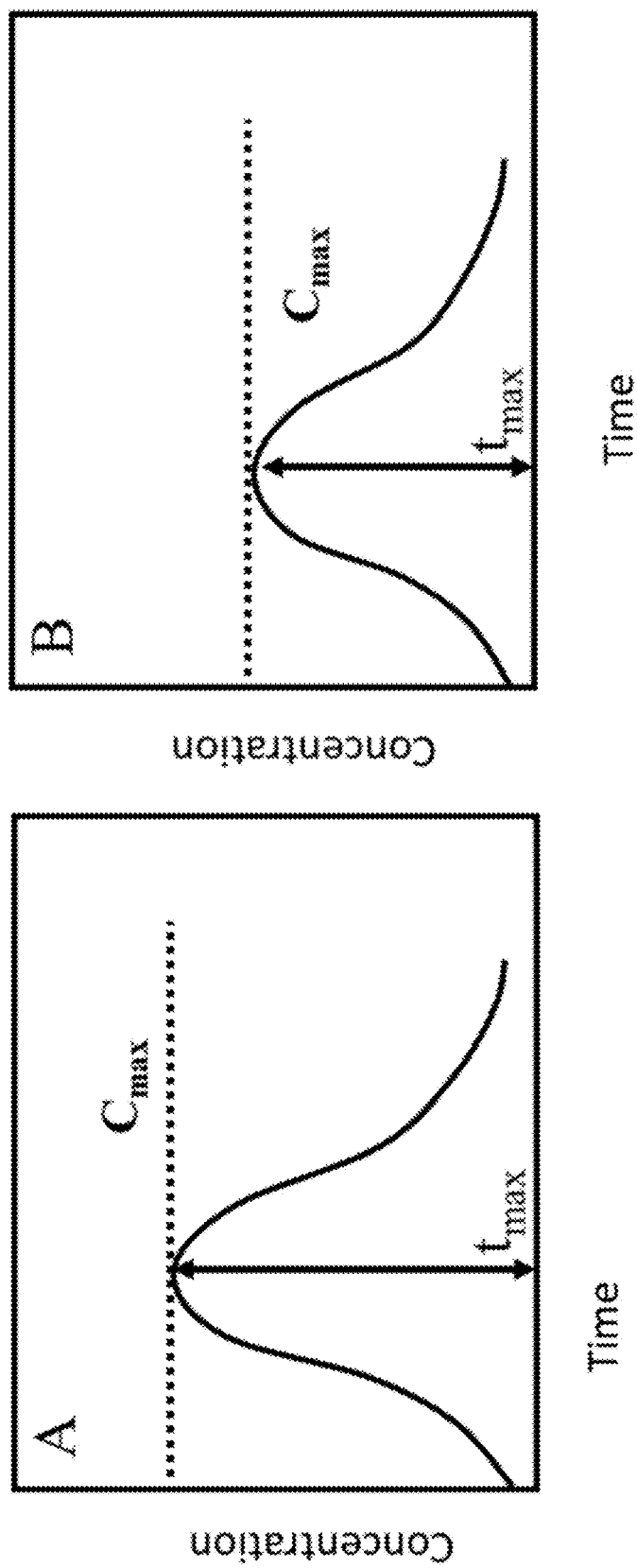
FIGS. 3A and 3B are plot of antimicrobial concentration vs. time for two dosage regimens.

By reducing the MIC for a given antimicrobial by application of therapeutic light, a lower dosage of the antimicrobial may be used, or the dose titrated for planktonic bacteria may be useful in biofilm producing strains. For example, FIG. 3A shows a plot the antimicrobial concentration curve required to resolve a microbial infection without the use of near infrared treatment light. FIG. 3A shows a plot the antimicrobial concentration curve required to resolve a microbial infection following application of near infrared treatment light. Because the treatment light reduces the MIC for the antimicrobial, a lower dose may be used, corresponding to a reduced maximum concentration $C_{max}$ for the curve shown in FIG. 3B relative to that of the curve shown in FIG. 3B.

The following describes how basic Pharmacokinetic and Pharmacodynamic principles for antimicrobial drugs and how therapy will be augmented under PMBIC. Antimicrobial Pharmacokinetics (PK) determines the fate of an antibiotic or antifungal drug from the moment that it is administered to a patient until the endpoint, at which it is completely eliminated from the body. Pharmacokinetics further describes the mechanisms of antimicrobial absorption and antimicrobial distribution, in addition to any chemical changes in drug in the body and the further effects of metabolites of the antimicrobial and various routes of excretion from the body. PMBIC will enhance PK tolerance, as lower concentrations of a drug available in the system, after partial metabolism and excretion, would continue to be therapeutically beneficial because of inhibited acceleration or intensification of biofilm production in the targeted organisms.

Antimicrobial Pharmacodynamics (PD) describes the biochemical effects of an antibiotic or antifungal drug on a microorganism and the mechanisms of the drugs action along with the temporal and dynamic relationship between an antibiotic or antifungal drugs concentration and effect. PMBIC will enhance PD effects as lower concentrations of a drug would continue to be therapeutically beneficial with inhibited acceleration or intensification of biofilm production in the targeted organisms.

The Minimum Inhibitory Concentration (MIC) is the lowest concentration of an antibiotic or antifungal drug that will inhibit the visible growth of a bacteria or fungus after an overnight incubation. MICs are imperative in diagnostic medicine, to confirm any resistance of the bacteria or fungus to an antibiotic or antifungal drug, and also to observe activity of new antimicrobial drugs. A lower MIC for a bacteria or fungus is an indication of a better or more potent antimicrobial agent. Microbial isolates of a particular species will have varying MICs; sensitive strains will have low MICs, and resistant strains that produce biofilm will have high MICs. PMBIC will lower the MIC of biofilm producing organisms, as lower concentrations of a drug would continue to be therapeutically beneficial with inhibited acceleration or intensification of biofilm production in the targeted organisms.

The Minimum Bactericidal (or fungicidal) Concentration (MBC) is the lowest concentration of antibiotic or antifungal drug required to kill a particular bacteria or fungus. This value may be determined from broth dilution MIC tests by sub-culturing the organism to agar media without antibiotics. Antibiotic or antifungal drugs are usually regarded as bactericidal or fungicidal if the MBC is no more than four times the MIC.

Application of PMBIC of light will lower the MBC of biofilm producing organisms, as lower concentrations of a drug would continue to be therapeutically beneficial with inhibited acceleration or intensification of biofilm production in the targeted organisms.

A bacteriostatic or fungistatic antimicrobial is a biological agent that stops bacteria and/or fungi from reproducing. A bacteriacidal or fungicidal antimicrobial is a biological agent that kills bacteria and/or fungi. Bacteriostatic or fungistatic antimicrobials function by limiting the growth of organisms by interfering with protein production, DNA replication, or other aspects of cellular metabolism. Bacteriostatic or fungistatic antimicrobials must work together with the host immune system to remove the microorganisms from the body. There is not always a precise distinction between "static" and "cidal" antimicrobials. This is because a high concentration of certain bacteriostatic or fungistatic antimicrobials are also "cidal" whereas low concentrations of some bacteriacidal or fungicidal antimicrobials are "static." PMBIC will lower the amount of "static" antimicrobials necessary to work together with the host immune system to be "cidal" and will lower the amount of "cidal" antimicrobials necessary to be "static".

The Breakpoint MIC is the MIC that will separate sensitive and resistant strains, and distinguish two disparate populations: one population with MICs at less than the breakpoint (i.e., susceptible) and one with MICs at more than the breakpoint (i.e., resistant). PMBIC will lower the Breakpoint MIC of biofilm producing organisms, as lower concentrations of a drug would continue to be therapeutically beneficial with inhibited acceleration or intensification of biofilm production in the targeted organisms.

In antimicrobial pharmacokinetics, the area under the curve (AUC) is the area under the curve in a plot of antibiotic or antifungal drug concentration in plasma against time for systemic antimicrobials. PMBIC will shrink the necessary AUC of biofilm producing organisms, as lower concentrations of a drug would continue to be therapeutically beneficial with inhibited acceleration or intensification of biofilm production in the targeted organisms.

The parameter of $C_{max}$ defines the highest observed serum concentration of an antibiotic or antifungal drug concentration against time. The $C_{max}$ is determined within the dosing interval to the patient. Therefore, if 2 doses of a given drug are administered, there will be a $C_{max}$ value following each dose administration. PMBIC will lower the necessary $C_{max}$ of biofilm producing organisms, as lower concentrations of a drug would continue to be therapeutically beneficial with inhibited acceleration or intensification of biofilm production in the targeted organisms.

The parameter of $t_{max}$ defines the time of the sample identified as $C_{max}$. The AUC (from zero to long times where the antimicrobial concentration is negligible) symbolizes the total amount of an antibacterial or antifungal drug absorbed by the body, regardless of the rate of absorption. This is a valuable tool, when one is attempting to determine if two formulations of the same dose (i.e. capsule or tablet or IV) release the same dose of drug to the body.

A second value to this curve comes when monitoring the therapeutic value vs toxicity of various antimicrobial drugs. AUC is important to calculate the average concentration of an antibacterial or antifungal drug over a time interval, AUC/t and the value is also discussed when examining drug elimination from the body. In strict mathematical terms, the amount of a drug eliminated by the body=clearance (volume/time)*AUC(mass*time/volume).

After a given dose of a bactericidal or fungicidal drug, the organism count may well decline in the early portion of the temporal dosing interval, when the levels of the non-protein bound antibacterial or antifungal drug exceed the MBC as a result of the drug effects on the organism and the patients host defenses. Once unbound drug levels then decrease to less than the MBC but still exceed the MIC, the organism total may remain stable or continue to decline as a consequence of the patients host defenses. PMBIC will prevent a biofilm augmented increase in the MBC and MIC of the targeted organisms.

With each of the above described parameters, selective irradiation with infrared light at selected NIMELS wavelengths (as described in detail herein) will lower the MIC of bacterial and fungal pathogens. Also, the exposure time and amount of antimicrobial necessary to treat infectious pathogens will be less than presently needed (than without irradiation) to meet the specific PK/PD treatment parameters for efficacious therapy.

Reduction of Antimicrobial Resistance

Not wishing to be bound by theory, it is believed that that antimicrobial resistant mutant subpopulations present before the initiation of antimicrobial treatment are then augmented and amplified during antimicrobial therapy when antimicrobial concentrations fall within a specific range that is further termed the mutant selection window (MSW).

Figure 4:
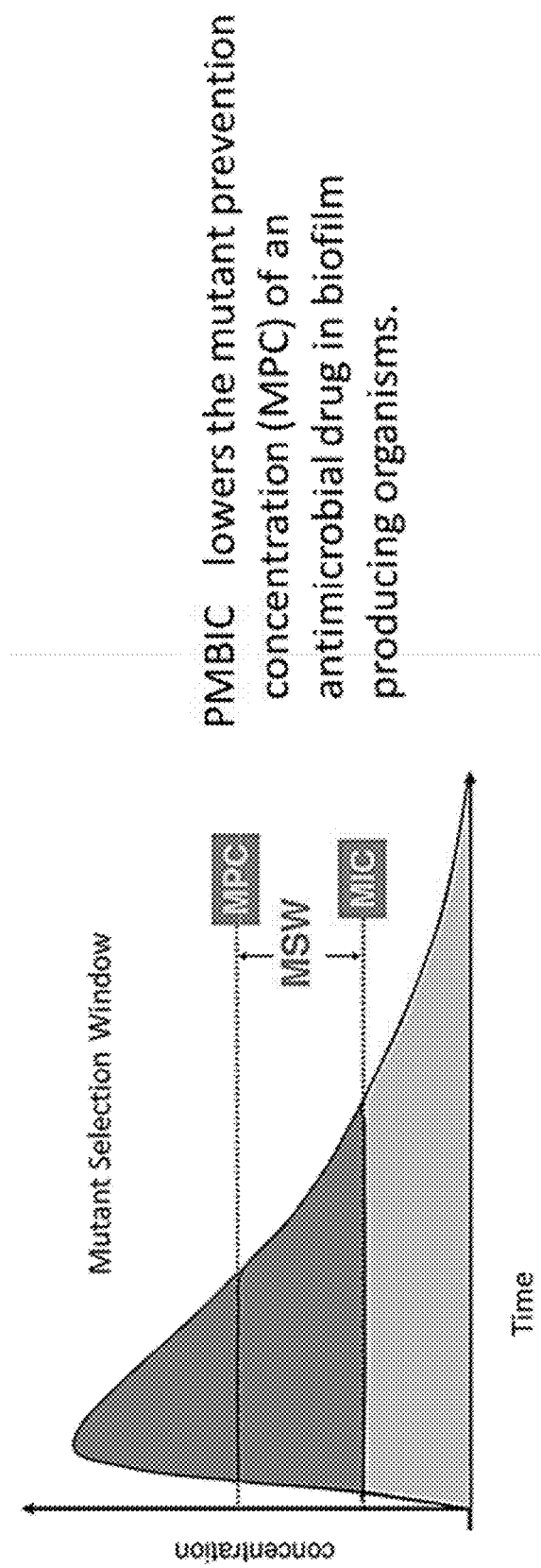
FIG. 4 is a plot of antimicrobial concentration vs. time illustrating a lowering of the mutant selection window after therapy with the photo-biologic minimum biofilm inhibitory concentration of infrared light.

For example, FIG. 4 shows a plot of antimicrobial concentration as a function of time during a typical treatment. The upper boundary of the MSW is the MIC of the least antimicrobial susceptible mutant subpopulation, designated as the mutant prevention concentration (MPC). The lower boundary of the MSW is the lowest concentration of the antimicrobial that exerts selective pressure on the organism, frequently approximated by the minimal antimicrobial concentration that inhibits colony formation by 99% (MIC99).

Two distinct doctrines arise from the foregoing. First, traditional dosing approaches of antimicrobials, that try to block drug resistance by killing susceptible cells will allow augmented and amplified antimicrobial resistant pathogens, when a drug concentration is placed inside the MSW window. Second, maintaining antimicrobial concentrations beyond the selection window (MSW) throughout antimicrobial therapy should rigorously limit the acquisition of drug resistance, in a similar manner that maintaining concentrations above the MIC blocks the growth of drug-susceptible cells.

These ideas are essential to the design of various anti-mutant dosing strategies for antimicrobial therapy of bacterial and fungal populations that are not already fully resistant to a given antimicrobial drug.

However, the therapeutic application of the above concepts using drug treatment alone may be difficult or impossible, e.g., because the antimicrobial doses required to restrict drug resistance are higher than are generally needed to cure patients, and potentially toxic.

In some embodiment, application of PMBIC prior to or concurrent with drug therapy will lower the toxicity concerns in treating biofilm producing organisms. This will occur by allowing greater therapeutic latitude in maintaining antimicrobial concentrations beyond the selection window with a lowered MPC throughout antimicrobial therapy, with inhibited acceleration or intensification of biofilm production in the targeted organisms.

Figure 5:
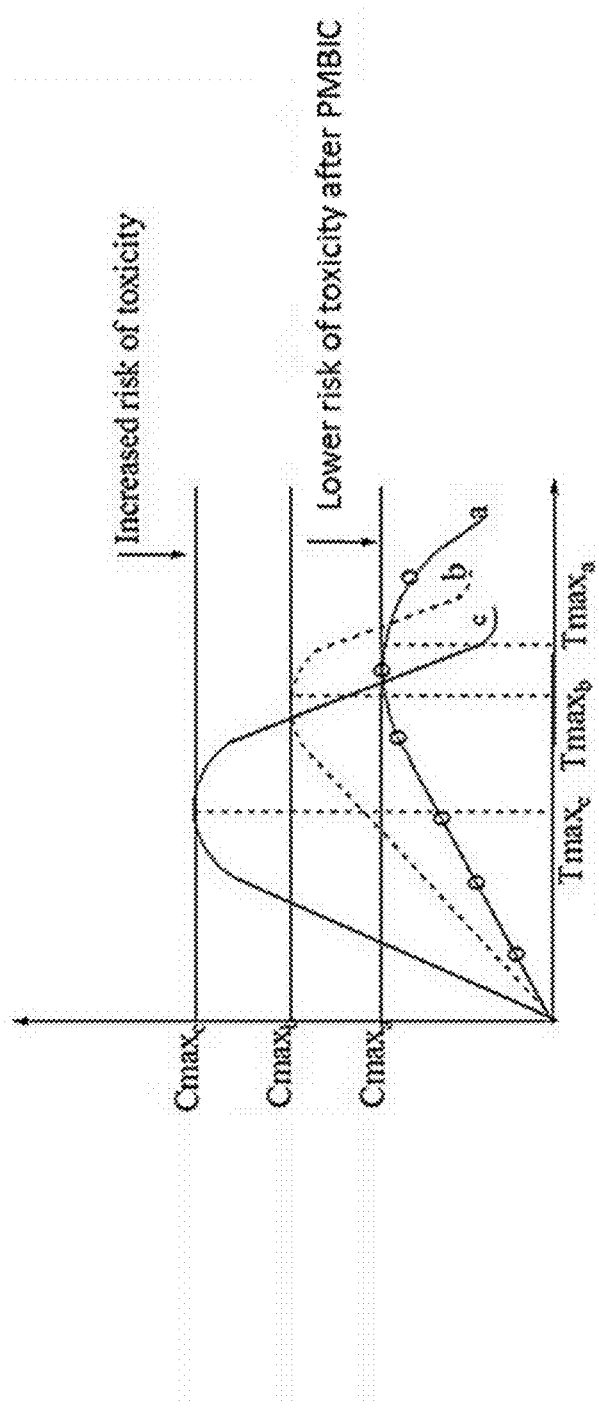
FIG. 5 shows three plots of concentration versus time for three treatment regimens. The solid line plot shows a drug-only treatment regimen with high maximum concentration and short time to maximum concentration. The circle-line plot shows a treatment regimen following PMBIC light application with a low maximum concentration and low time to maximum concentration. The dashed plot shows an intermediate treatment regimen with an intermediate maximum concentration and intermediate time to maximum concentration

For example, FIG. 5 shows three plots of concentration versus time for three treatment regimens. The solid line plot shows a drug-only treatment regimen that requires a high maximum concentration $C_{maxa}$ and short time to maximum concentration $T_{maxa}$. The circle-line plot shows a treatment regimen following PMBIC light application. Because the PMBIC application lowers the MIC for the microbial population, the treatment regiment may be effective with a lower maximum concentration $C_{maxe}$ and lower time to maximum concentration $T_{maxe}$. Accordingly, this modified treatment regimen will advantageously exhibit lower toxicity than the drug-only treatment regiment.

Figure 6:
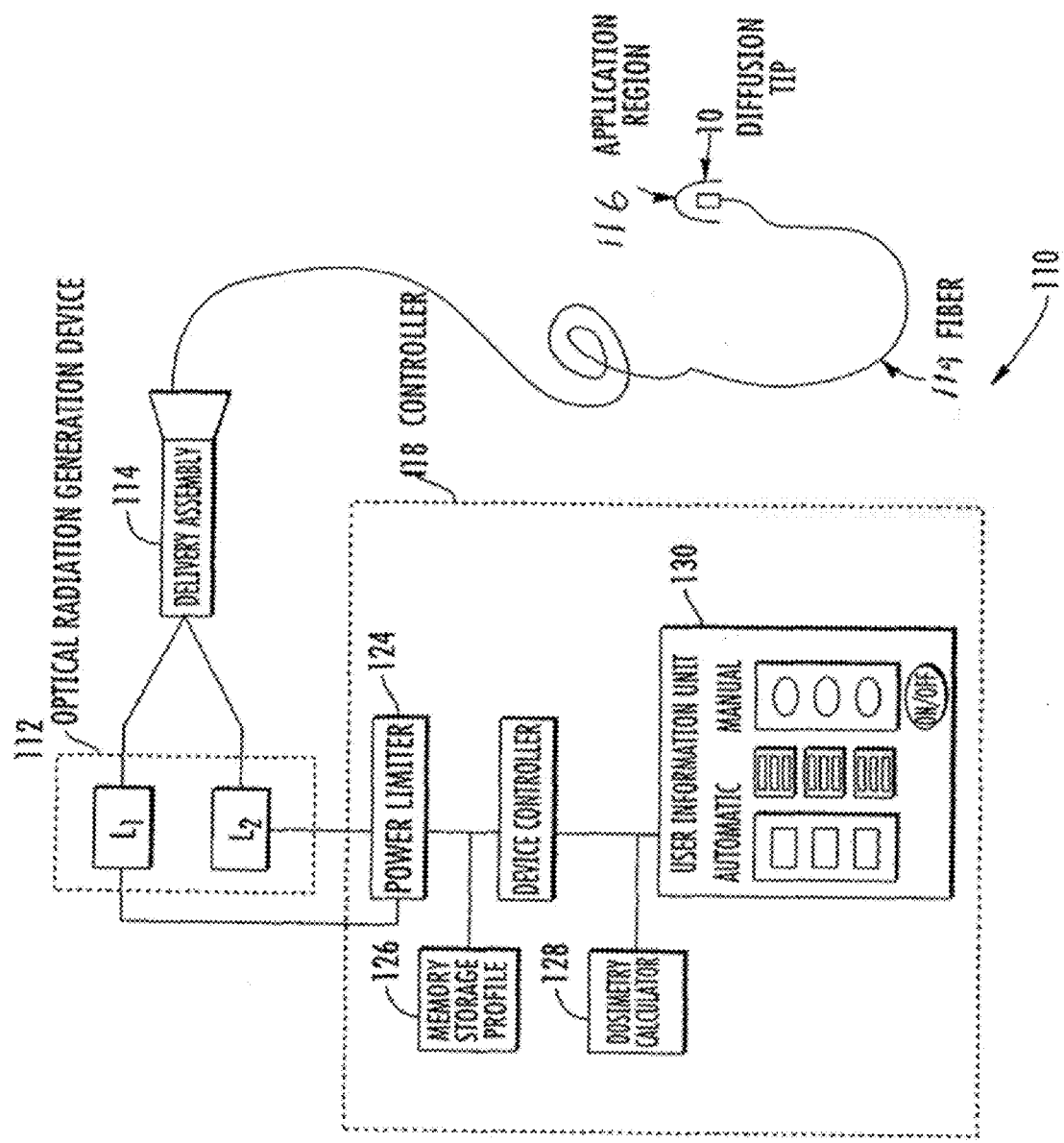
FIG. 6 is a schematic diagram for a NIMELS light therapy system.

For clarity, the dashed plot in FIG. 5 shows an intermediate treatment regimen with an intermediate maximum concentration $C_{maxb}$ and intermediate time to maximum concentration $T_{maxb}$ Exemplary NIMELS Systems FIG. 6 illustrates a schematic diagram of a therapeutic radiation treatment device according one embodiment of the present disclosure. The therapeutic system 110 includes an optical radiation generation device 112, a delivery assembly 114, an application region 116, and a controller 118.

According one aspect of the present disclosure, the optical radiation generation device (source) includes one or more light sources, L1 and L2. The light sources may be, e.g., lasers (as shown) or light emitting diodes. A suitable laser may be selected based on a desired degree of coherence. In exemplary embodiments, a therapeutic system can include at least one diode laser configured and arranged to produce an output in the near infrared region. Suitable diode lasers can include semiconductor materials for producing radiation in desired wavelength ranges, e.g., 850 nm to 900 nm and 905 nm to 945 nm. Suitable diode laser configurations can include cleave-coupled, distributed feedback, distributed Bragg reflector, vertical cavity surface emitting lasers (VCSELS), etc.

With continued reference to FIG. 6, in certain embodiments the delivery assembly 114 can generate a flat-top energy profile for uniform distribution of energy over large areas. For example, a diffuser tip 10, may be included which diffuses treatment light with a uniform cylindrical energy profile in an application region 116 (e.g. a nasal cavity).

As noted, the optical radiation generation device 112 can include one or more light sources such as lasers, e.g., laser oscillators L1 and L2. In exemplary embodiments, one laser oscillator can be configured to emit optical radiation in a first wavelength range of 850 nm to 900 nm (or any subrange thereof, e.g., 865 nm to 875 nm), and the other laser oscillator can be configured to emit radiation in a second wavelength range of 905 nm to 945 nm (or any subrange thereof, e.g., 925 nm to 930 nm). In certain embodiments, one laser oscillator is configured to emit radiation in a first wavelength range of 865 nm to 875 nm, and the other laser oscillator 28 is configured to emit radiation in a second wavelength range of 925 nm to 935 nm. The geometry or configuration of the individual laser oscillators may be selected as desired, and the selection may be based on the intensity distributions produced by a particular oscillator geometry or configuration.

With continued reference to FIG. 6, in certain embodiments, the delivery assembly 114 includes an elongated flexible optical fiber 118 adapted for delivery of the dual wavelength radiation from the oscillators 26 and 28 to diffuser tip 10 to illuminate the application region 116. The delivery assembly 14 may have different formats (e.g., including safety features to prevent thermal damage) based on the application requirements. For example, in one form, the delivery assembly 114 or a portion thereof (e.g. tip 10) may be constructed with a size and with a shape for inserting into a patient's body. In alternate forms, the delivery assembly 114 may be constructed with a conical shape for emitting radiation in a diverging-conical manner to apply the radiation to a relatively large area. Hollow waveguides may be used for the delivery assembly 14 in certain embodiments. Other size and shapes of the delivery assembly 14 may also be employed based on the requirements of the application site, in exemplary embodiments, the delivery assembly 114 can be configured for free space or free beam application of the optical radiation, e.g., making use of available transmission through tissue at NIMELS wavelengths described herein. For example, at wavelengths of about 930 nm (and to a similar degree, about 870 nm), the applied optical radiation can penetrate patient tissue by up to 1 cm or more. Such embodiments may be particularly well suited for use with in vivo medical devices.

In an exemplary embodiment, the controller 118 includes a power limiter 124 connected to the laser oscillators L1 and L2 for controlling the dosage of the radiation transmitted through the application region 116, such that the time integral of the power density of the transmitted radiation per unit area is below a predetermined threshold, which is set up to prevent damages to the healthy tissue at the application site. The controller 118 may further include a memory 126 for storing treatment information of patients. The stored information of a particular patient may include, but not limited to, dosage of radiation, (for example, including which wavelength, power density, treatment time, skin pigmentation parameters, etc.) and application site information (for example, including type of treatment site (lesion, cancer, etc.), size, depth, etc.).

In an exemplar) embodiment, the memory 126 may also be used to store information of different types of diseases and the treatment profile, for example, the pattern of the radiation and the dosage of the radiation, associated with a particular type of disease. The controller 118 may further include a dosimetry calculator 128 to calculate the dosage needed for a particular patient based on the application type and other application site information input into the controller by a physician. In one form, the controller 118 further includes an imaging system for imaging the application site. The imaging system gathers application site information based on the images of the application site and transfers the gathered information to the dosimetry calculator 128 for dosage calculation. A physician also can manually calculate and input information gathered from the images to the controller 118.

As shown in FIG. 6, the controller 118 may further include a control panel 130 through which, a physician can control the therapeutic system manually. The therapeutic system 10 also can be controlled by a computer, which has a control platform, for example, a WINDOWS™ based platform. The parameters such as pulse intensity, pulse width, pulse repetition rate of the optical radiation can be controlled through both the computer and the control panel 30.

In some embodiments, the therapeutic system 110 provides treatment light at the target region substantially in a first wavelength range from, e.g., about 865 nm to about 875 nm or a second radiation range having a wavelength from about 925 nm to about 935 nm (or any subrange thereof), or both wavelength ranges, at a dosimetry including power density of about 0.5 W/cm$^2$ to about 40 W/cm$^2$ (or any subrange thereof) and an energy density from about 200 J/cm$^2$ to about 700 J/cm$^2$ (or any subrange thereof), and a time duration of about 50 to about 720 seconds (or any subrange thereof).

In some embodiments, the controller is operatively connected to the light source and controls the light source to provide the treatment light at the target region substantially in a first wavelength range from, e.g., 865 nm to 875 nm (or any subrange thereof) and a second wavelength range having a wavelength from 925 nm to 935 nm (or any subrange thereof), and at a dosimetry including power density of about 0.5 W/cm$^2$ to about 40 W/cm$^2$ (or any subrange thereof) and an energy density from about 200 J/cm$^2$ to about 700 J/cm$^2$ (or any subrange thereof), and a time duration of about 50 to about 720 seconds (or any subrange thereof).

Figure 7A:
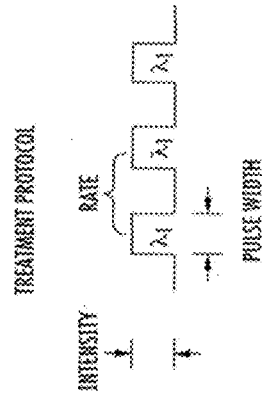
FIGS. 7a-7d show exemplary light therapy delivery options for the system of FIG. 6.
Figure 7B:
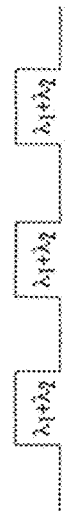
Figure 7C:
Figure 7D:

FIGS. 7a-7d show different temporal patterns of the optical radiation that can be delivered from the therapeutic system to the application site. The optical radiation can be delivered in one wavelength range only, for example, in the first wavelength range of 850 nm to 900 nm (or any subrange thereof, e.g., in the range of 865 nm to 875 nm), or in the second wavelength range of 905 nm to 945 nm (or any subrange thereof, e.g., in the range of 925 nm to 935 nm), as shown in FIG. 7a. The radiation in the first wavelength range and the radiation in the second wavelength range also can be multiplexed by a multiplex system installed in the optical radiation generation device 112 and delivered to the application site in a multiplexed form, as shown in FIG. 7b. In an alternative form, the radiation in the first wavelength range and the radiation in the second wavelength range can be applied to the application site simultaneously without passing through a multiplex system. FIG. 7c shows that the optical radiation can be delivered in an intermission-alternating manner, for example, a first pulse in the first wavelength range, a second pulse in the second wavelength range, a third pulse in the first wavelength range again, and a fourth pulse in the second wavelength range again, and so on. The interval can be CW (Continuous Wave), one pulse as shown in FIG. 7c, or two or more pulses (not shown). FIG. 7d shows another pattern in which the application site is first treated by radiation in one of the two wavelength ranges, for example, the first wavelength range, and then treated by radiation in the other wavelength range. The treatment pattern can be selected by the physician based on the type, and other information of the application site.

Exemplary Treatment Method

Figure 8:
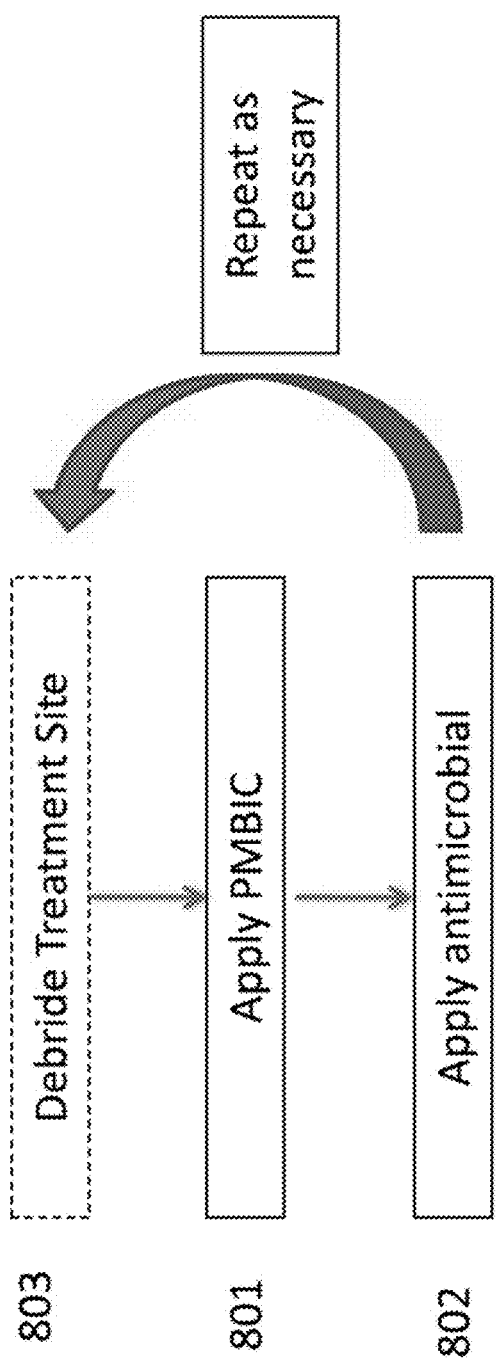
FIG. 8 is a flow chart for an exemplary treatment method.

FIG. 8 shows an exemplary method for inhibiting biofilm formation at a treatment site that includes a pathogenic microbial (e.g., bacterial or fungal) population. Step 801 includes applying a photo-biologic minimum biofilm inhibitory concentration (PMBIC) of infrared light to the treatment site.

The treatment site may include a region of the body of a human or animal subject (e.g., a wound site). In some embodiments, the treatment site may include a region of a medical device, e.g., a medical implant prior to or after implantation in a subject.

In some embodiments, the PMBIC of infrared light may be generated and delivered using a NIMELS system of the type described above with reference to FIG. 6.

In some embodiments, applying the PMBIC of infrared light includes providing treatment light at the treatment site substantially in a first wavelength range from 865 nm to 875 nm (or any subrange thereof) and/or a second wavelength range having a wavelength from 925 nm to 935 nm (or any subrange thereof), and at a dosimetry including power density of about 0.5 W/cm$^2$ to about 5 W/cm$^2$ (or any subrange thereof) and an energy density from about 200 J/cm$^2$ to about 700 J/cm$^2$ (or any subrange thereof). In some embodiments applying the PMBIC of infrared light comprises providing the treatment light for a period of about 50 to about 720 seconds (or any subrange thereof).

In some embodiments, the PMBIC of treatment light for a selected antimicrobial population and antimicrobial agent may be determined in a straightforward fashion using in vitro tests of the type described in Examples I and II presented below.

In some embodiments, applying the PMBIC of infrared light comprises applying a dose of infrared light that is sub-lethal to the pathogenic microbial population. In some embodiments, the PMBIC of infrared light is at a dosage selected to prevent damage, such as thermal damage, at the treatment site.

Step 802 includes applying an antimicrobial agent (e.g., an antifungal or antimicrobial agent) to the treatment site. Step 802 may be performed after or concurrently with the step 801 of applying the PMBIC.

In some embodiments, the antimicrobial agent is characterized by an indicated dosing regimen (e.g., as approved by a suitable regulator agency such as the U.S. Food and Drug Administration or European Medicines Agency). Applying the antimicrobial agent to the treatment site may include applying the antimicrobial agent with a modified dosing regimen different from the indicated dosing regimen.

In some embodiments, the antimicrobial agent includes or is delivered by metal ion impregnated bandages or wound dressings (such as but not limited to silver ions) and/or antiseptic impregnated bandages and/or wound dressings (such as but not limited to Chlorhexidine or Iodophore) with an indicated bandage or dressing (e.g., as approved by a suitable regulator agency such as the U.S. Food and Drug Administration or European Medicines Agency).

In some embodiments, the antimicrobial agent includes or is delivered by metal ion impregnated catheters (such as but not limited to silver ions) and/or antiseptic impregnated catheters (such as but not limited to Chlorhexidine or Iodophore) with an indicated catheter (e.g., as approved by a suitable regulator agency such as the U.S. Food and Drug Administration or European Medicines Agency).

In some embodiments, the antimicrobial agent is includes or is delivered by antibiotic and/or antifungal impregnated bandages or wound dressings with an indicated bandage or dressing (e.g., as approved by a suitable regulator agency such as the U.S. Food and Drug Administration or European Medicines Agency).

For example, in some embodiments, the indicated dosing regimen has a maximum concentration $C_{maxi}$, the modified dosing regimen has a maximum concentration $C_{max}$, and $C_{max} < C_{maxi}$ (e.g., as shown in FIGS. 3A and 3B and FIG. 5).

In some embodiments, the indicated dosing regimen is characterized by a first concentration/time curve, the modified dosing regimen is characterized by a second concentration/time curve, and the area under the first concentration/time curve is greater than the area under the second concentration/time curve (e.g., as shown in FIGS. 3A and 3B and FIG. 5).

In some embodiments, the modified dosing regimen is characterized by a lower toxicity than the indicated dosing regimen.

In some embodiments, applying the PMBIC of infrared light comprises reducing the minimum inhibitory concentration of the antimicrobial agent for the pathogenic microbial population. In some embodiments, applying the PMBIC of infrared light includes inhibiting accelerations or intensifications in biofilm production by the pathogenic microbial population. In some embodiments, applying the PMBIC of infrared light includes lowering mutant prevention concentration of the antimicrobial agent for the pathogenic microbial population. In some embodiments, applying the PMBIC of infrared light includes reducing the break point minimum inhibitory concentration (i.e. the MIC that will separate sensitive and resistant strains) of the antimicrobial agent for the pathogenic microbial population. In some embodiments, applying the PMBIC of infrared light includes reducing the minimum microbicidal concentration of the antimicrobial agent for the pathogenic microbial population.

In some embodiments, e.g., where the treatment site comprises a wound, the method may include an optional step 803 of debriding the wound, e.g., prior to applying the PMBIC of infrared light.

PMBIC and Nasal Decolonization Therapy

A recent study by Ogura et al. (2013) presents a very troubling picture of the MRSA resistance spectrum to Mupirocin. Ogura collected samples from patients scheduled for surgery at Nagoya City University Hospital (Nagoya, Japan) that were screened for nasal carriage of MRSA. Following a positive nasal culture, patient's positive for MRSA then received treatment with the topical antibiotic mupirocin. The spectrum of resistance to mupirocin they found was separated by phenotype into either low-level or high-level resistance. Low level resistance was defined in MRSA isolates as MICs of 8-256 µg/ml and isolates >256 µg/ml were high-level resistance. Ogura tested 38 different patient samples.

Of these patients, 14 were successfully eradicated of their MRSA with Mupirocin treatment, and all successful eradication samples measured MICs of </=1 µg/ml. Of these successful eradication samples, only one was determined to be a biofilm producing strain.

Twenty four of the 38 patients were MRSA eradication failures with 14 of the samples measuring MICs of <=1 µg/ml, six of the samples measuring MICs of 2 µg/ml, and one failure each at 4, 16, 32, and 64 µg/ml.

Of highest importance in this data, 17 of the samples that failed with MICs of </=2 µg/ml (i.e. Mupirocin susceptible isolates) were biofilm producing strains. Most recently, Melake et al. (2014) found that 40 of 49 (83%) nasal MRSA isolates in Egyptian patients had the ability to form biofilm. They stated that this reveals an "alarming rate" of biofilm formation, and the selection of antibiotics on the basis of traditional methods will fail to predict efficacy in biofilm producing species.

As shown in the examples below, combined light a drug treatment techniques of the types described herein may be used mitigate or reduce the above described disadvantages of drug-only treatment of biofilm producing microbial pathogens.

Example I

Establishing PMBIC for MRSA Challenged with Mupirocin

The applicant has established a photo-biologic Minimum Biofilm Inhibitory Concentration (PMBIC) with the NIMELS technology.

Figure 9:
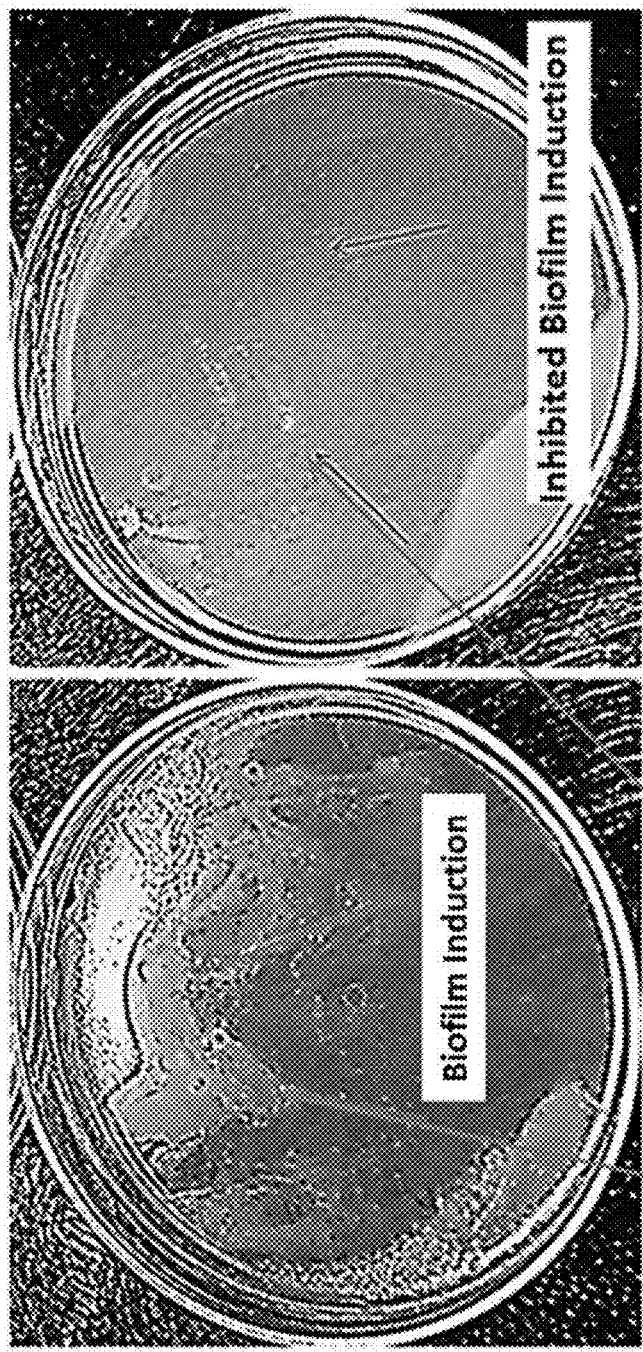
FIG. 9 shows the results of an experiment to establish a photo-biologic Minimum Biofilm Inhibitory Concentration (PMBIC) with the NIMELS technology, with relation to biofilm producing strain #1 of MRSA that was challenged with Mupirocin.

As shown in FIG. 9, left panel, a biofilm producing strains of MRSA was challenged with Mupirocin. The applicant tested the effect in vitro against MRSA with the topical drug Mupirocin. As is evident from in FIG. 9, left panel, the drug treatment alone was not effective in preventing biofilm formation.

TABLE I

| Parameters | Output Power (W) | Beam Spot (cm) | Area of Spot (cm2) | Time (sec) | Total Energy Joules | Energy Density (J/cm$^2$) | Power Density (W/cm$^2$) |
|---|---|---|---|---|---|---|---|
| NIMELS DOSIMETRY | | | | | | | |
| Test (1) 870 at 5 W and 930 at 5 W for 12 min followed by | 10.0 | 1.5 | 1.77 | 720 | 7200 | 4074 | 5.66 |
| Test (1) 930 at 8 W for 5 min | 8.0 | 1.5 | 1.77 | 360 | 2880 | 1630 | 4.53 |
| Test (2) 870 at 5 W and 930 at 5 W for 12 min followed by | 10.0 | 1.5 | 1.77 | 720 | 7200 | 4074 | 5.66 |
| Test (2) 930 at 8 W for 6 min | 8.0 | 1.5 | 1.77 | 360 | 2880 | 1630 | 4.53 |
| Test (3) 870 at 5 W and 930 at 5 W for 12 min followed by | 10.0 | 1.5 | 1.77 | 720 | 7200 | 4074 | 5.66 |
| Test (3) 930 at 8 W for 6 min | 8.0 | 1.5 | 1.77 | 360 | 2880 | 1630 | 4.53 |
| Test (4) 870 at 5.5 W and 930 at 5.5 W for 12 min followed by | 11.0 | 1.5 | 1.77 | 720 | 7920 | 4482 | 6.22 |
| Test (4) 930 at 8 W for 6 min | 8.0 | 1.5 | 1.77 | 360 | 2880 | 1630 | 4.53 |
| Test (5) 870 at 5.5 W and 930 at 5.5 W for 12 min followed by | 11.0 | 1.5 | 1.77 | 720 | 7920 | 4482 | 6.22 |
| Test (5) 930 at 8 W for 6 min | 8.0 | 1.5 | 1.77 | 360 | 2880 | 1630 | 4.53 |
| Test (6) 870 at 5.5 W and 930 at 5.5 W for 12 min followed by | 11.0 | 1.5 | 1.77 | 720 | 7920 | 4482 | 6.22 |
| Test (6) 930 at 8 W for 6 min | 8.0 | 1.5 | 1.77 | 360 | 2880 | 1630 | 4.53 |
| Test (7) 870 at 5 W and 930 at 5 W for 14 min followed by | 10.0 | 1.5 | 1.77 | 840 | 8400 | 4753 | 5.66 |
| Test (7) 930 at 7 W for 8 min | 7.0 | 1.5 | 1.77 | 480 | 3360 | 1901 | 3.96 |
| Test (8) 870 at 5 W and 930 at 5 W for 14 min followed by | 11.0 | 1.5 | 1.77 | 840 | 9240 | 5229 | 6.22 |
| Test (8) 930 at 7 W for 8 min | 7.0 | 1.5 | 1.77 | 480 | 3360 | 1901 | 3.96 |

Figure 10:
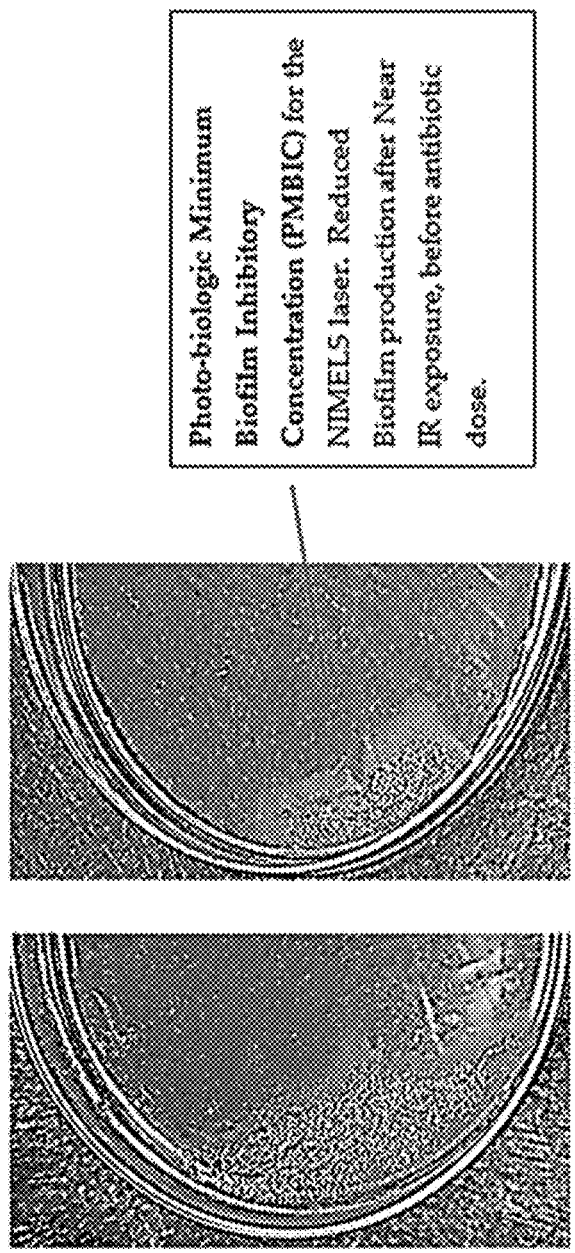
FIG. 10 shows the results of an experiment to establish a photo-biologic Minimum Biofilm Inhibitory Concentration (PMBIC) with the NIMELS technology, with relation to biofilm producing strain #2 of MRSA that was challenged with Mupirocin.

As shown in the representative results of FIG. 9, right panel, and FIG. 10, it was found that when sub-lethal "light doses" of infrared light generated using the NIMELS technology were applied prior to application of Mupricocin the drug treatment did in fact inhibit biofilm production in two different samples of MRSA. Dosimetry for the NIMELS infrared light is shown in Table I above. Accordingly, the PMBIC for MRSA challenged with Mupirocin was established using a straightforward testing protocol.

The following examples described herein analyze methods of utilizing PMBIC from research data points to enable the methods of the current patent application. The ensuing data progression is applied logically with a thought experiment, that will distill the information through the "prism" of PMBIC methods to conclude that, in various embodiments, an improvement may be realized, and optimization of antimicrobial therapy may occur, based on selected infrared treatment for the decolonization of human wounds (such as a diabetic foot wound) and other tissues.

Wound biofilm formation begins with the planktonic bacterial attachment to the surface of a cell in the wound. Once this bacterium divides a few times, it leads to a micro-colony and then begins the production of a biofilm matrix. Next, additional bacteria can then be conscripted to join the growing biofilm, which will then further expand through cell division and enhanced construction of biofilm matrix elements. These matrix elements are polysaccharides, proteins and DNA that are dispersed amongst the bacterial cells in a non-homogeneous arrangement. This creates different chemical and physical sections of a mature biofilm matrix.

Once the planktonic bacteria attach to the surface of a cell in the wound, they begin to divide and quickly produce a micro-colony. This micro-colony then begins the production of a biofilm matrix.

Finally, the bacteria then multiply on the surface and synthesize extracellular polymeric substance (EPS), which defines the second stage of biofilm development, also known as maturation. The EPS, which is composed of polysaccharides, proteins, deoxyribonucleic acid (DNA), ribonucleic acid (RNA), and lipids, is important because it offers biofilm protection as well as mediates (a) cell-to-cell and (b) cell-surface interactions that allow for biofilm stabilization.

Bacterial pathogens that produce biofilms are no longer considered "planktonic" as they have evolved to be able to survive in the adverse environments of the host immune response. These bacteria are protected by aggregation and dwell within the shielding of the carbohydrate matrix. This EPS matrix allows the aggregate communities of pathogens to (a) adhere to the wound surface and (b) substantially block the phagocytic activity of neutrophils. Therefore, pathogens in biofilms (found in chronic wounds) are also resistant to topical or systemic antibiotics. Finally, the presence of the biofilm in the wound causes a mechanical obstruction to wound healing by hindering keratinocyte migration.

Similar to the oral cavity (periodontal disease), chronic wounds do not successfully granulate and begin to heal because they stay inflamed from the constant response of the host immune system trying unsuccessfully to eliminate the biofilm. We now understand from Gardner et al, that chronic wounds contain far more Gm-species and LPS than previously thought. Inflammation in a healthy acute wound should recede, with granulation beginning to predominate within 7 days of the wound occurrence. Even though the absolute role that biofilms play is not yet clear, research indicates that biofilm in a wound not only maintains a constant immunological inflammatory response, but also continually releases planktonic bacteria into the environment.

Biofilm production keeps a wound in the inflammatory stage and prevents it from progressing to the granulation stage.

Conventional Treatment—Debridement of Wound and Biofilm

Sharp debridement is the primary treatment for pressure ulcers and diabetic foot ulcers (DFUs). During debridement, all of the devitalized tissues must be removed, with the attendant imbedded bacteria and biofilm.

Debridement is the mechanical method of attempting to stop the stimulation of the immune system from producing high levels of neutrophil and macrophage recruitment and cytokine secretion.

At each debridement, dressings are changed and the wound is also thoroughly cleansed. This procedure will also remove all loose slough, and is generally completed with a moistened gauze after attendant mechanical debridement. The ideal outcome of this procedure would be that the chronic inflammatory phase (which the wound is stuck in) with a preponderance of neutrophils (PMNs) would then be replaced with macrophages, that would stimulate angiogenesis and granulation.

Conventional Treatment—Antibiotics

Biofilms assist bacteria in evading the host's immune system, and some studies have estimated that bacteria in biofilms survive the use of antibacterial agents at concentrations 1000-1500 times higher than needed to eradicate planktonic bacteria of the same species.

Sedlacek and Walker examined subgingival bacteria in biofilm and planktonic states, and found that the vast majority of the bacteria in biofilms displayed higher MICs than planktonic cells.

There are many different mechanisms that biofilm bacteria employ to resist antibiotics. These include:
- subpopulations of specialized survivor cells;
- drug target modification or non-expression;
- less susceptible slow-growing bacteria;
- inadequate antibiotic penetration into the biofilm In patients with chronic wounds that are not clinically infected, systemic antibiotic therapy has been shown to be marginally successful with efficacy as low as 25-30%. In these same patients, topical antibiotics have also been widely used, with poor results as the wound biofilm bacteria are also far more resistant to topical antibiotics than planktonic bacteria.

Finally, Davis et al., investigated biofilm resistance to antibiotics by applying Mupirocin or triple antibiotic ointment after 15 minutes (representing planktonic bacteria) or 48 hours (representing biofilm bacteria) to a partial-thickness porcine wound that was inoculated with S. aureus. They found that both treatments reduced planktonic bacteria but had decreased efficacy on S. aureus biofilms.

The majority of conventional antibiotics have been created for the treatment of planktonic bacteria. Antibiotic treatment of planktonic bacteria (not biofilms), has been the foremost application of microbiology research from beginning with the advent of penicillin, until the modern characterization of biofilms in 1978.

Clinically, the implications of biofilms are serious, as bacteria in biofilms exhibit tolerance to most clinically relevant PK/PD dosing regimens of antibiotics, in spite of susceptibility of the same pathogens as planktonic cells.

Wound Debridement—a Window of Opportunity

During sharp wound debridement, biofilm, necrotic debris and biofilm is removed to aid in granulation and tissue healing. It has been clearly shown, that bacterial pathogens exhibiting a "biofilm phenotype" with in all of the various stages of biofilm phenotype will firmly adhere to the tissues of chronic wounds.

The biofilms are very heterogeneous and a biofilm's resistance increases as it matures. Any mechanical procedure that will physically disrupt and remove biofilm should create a 'window of opportunity' by (a) removing the bulk of mature biofilm and (b) increasing the metabolic rate of residual microorganisms as they attempt to re-grow the biofilm This window (during biofilm re-accumulation and maturation) is the time to maximize all supportive therapies, as the "tightly integrated" biofilm defences are no longer functioning and can be can be exploited. Phillips et al. (2010) reports that planktonic bacteria will quickly re-attach to tissue, and "strongly re-attach" within 2-4 hours.

Driving this point home an important study, Shultz et al (2010) examined "early reforming biofilm (24 hours old)" against older more mature biofilms. They researched whether 'young biofilm' phenotype was more susceptible to treatment including antibiotics, than mature biofilms. Shultz et al showed two important results:
- Planktonic seeded mammalian matrix (porcine explant) is susceptible to antibiotics during the first 48 hours of development into biofilm while the bioburden was still immature.
- In a mouse model they showed a 48-hour window for antibiotic susceptibility while the bioburden was still immature, before full biofilm formation.

The applicant has developed a method to treating diabetic foot ulcers (or other chronic wounds) that entails exposing a chronic wound or DFU to a PMBIC regimen after wound debridement, and then adding a systemic and/or topical antibiotic formulation (or antimicrobial impregnated bandage or dressing) that is suitable for treating a broad range of the Gm+ and Gm− bacterial and fungal pathogens found in the diabetic foot or other chronic wound.

Figure 11:
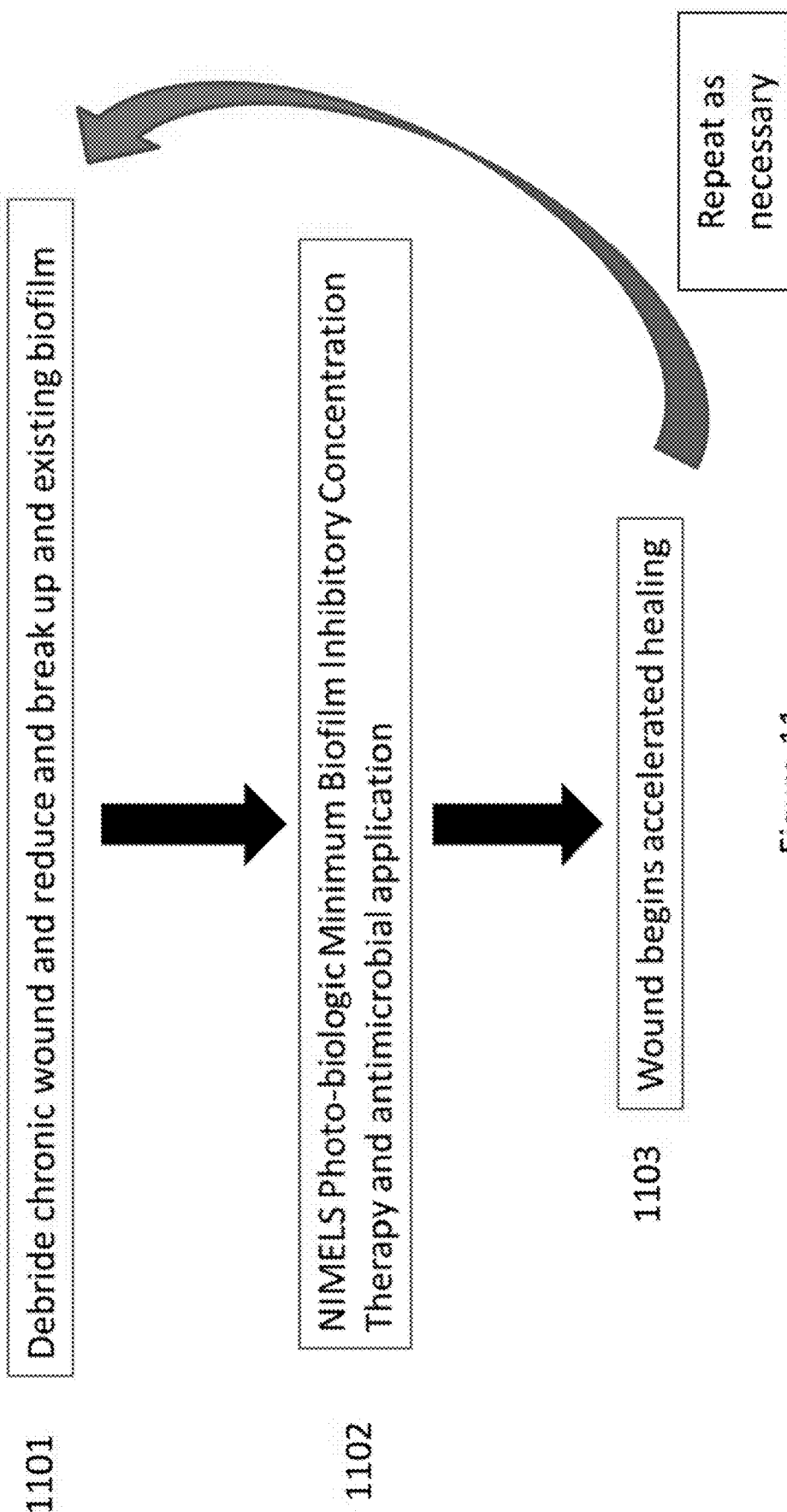
FIG. 11 is a flow chart for method of utilizing PMBIC with chronic wound therapy

For example, FIG. 11 shows an exemplary treatment method. In step 1101, a chronic wound is debrided to break up and reduce any biofilm present. In step 1102 a PBMIC of NIMELS light is applied to the wound, prior to or concurrently with application of an antimicrobial drug. In step 1103, the wound experiences accelerated healing. In some embodiments, the treatment method may be repeated as necessary. This approach (Debridement->Laser->Antibiotic) photo-biologically inhibits accelerations or intensifications in biofilm production, after the bacterial pathogens are challenged with the antimicrobial drug, leading to more microbial eradication and faster healing.

Example II

Establishing PMBIC for MRSA Challenged with Ciprofloxacin

Figure 12:
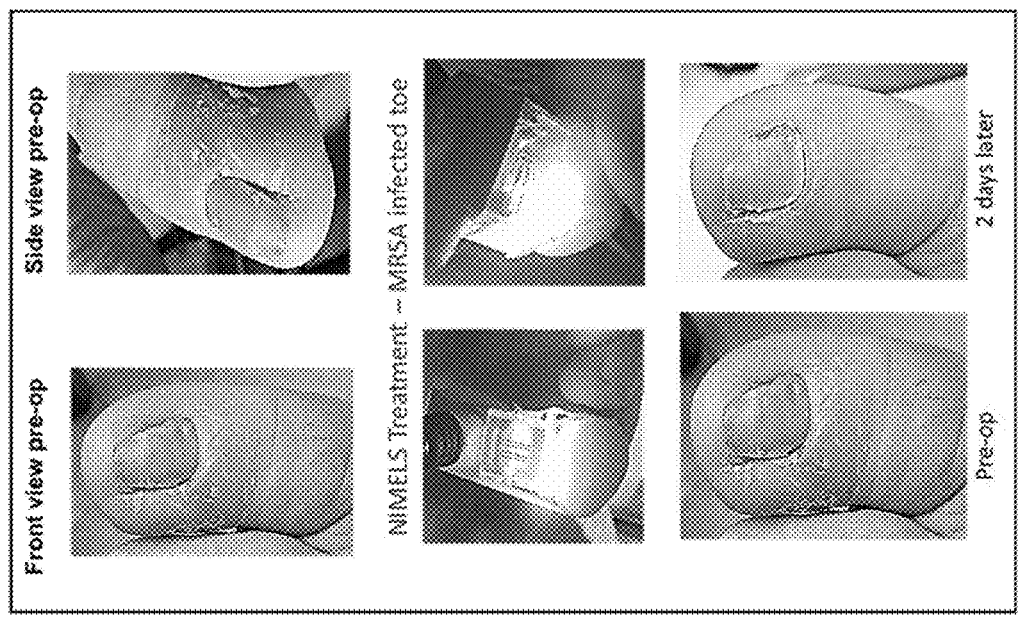
FIG. 12 shows the results of an experiment to establish a photo-biologic Minimum Biofilm Inhibitory Concentration (PMBIC) with the NIMELS technology, with relation a biofilm producing strain of MRSA in a patient that was challenged previously with Ciprofloxacin and then treated with PMBIC, followed by oral Doxycycline.
Figure 13:
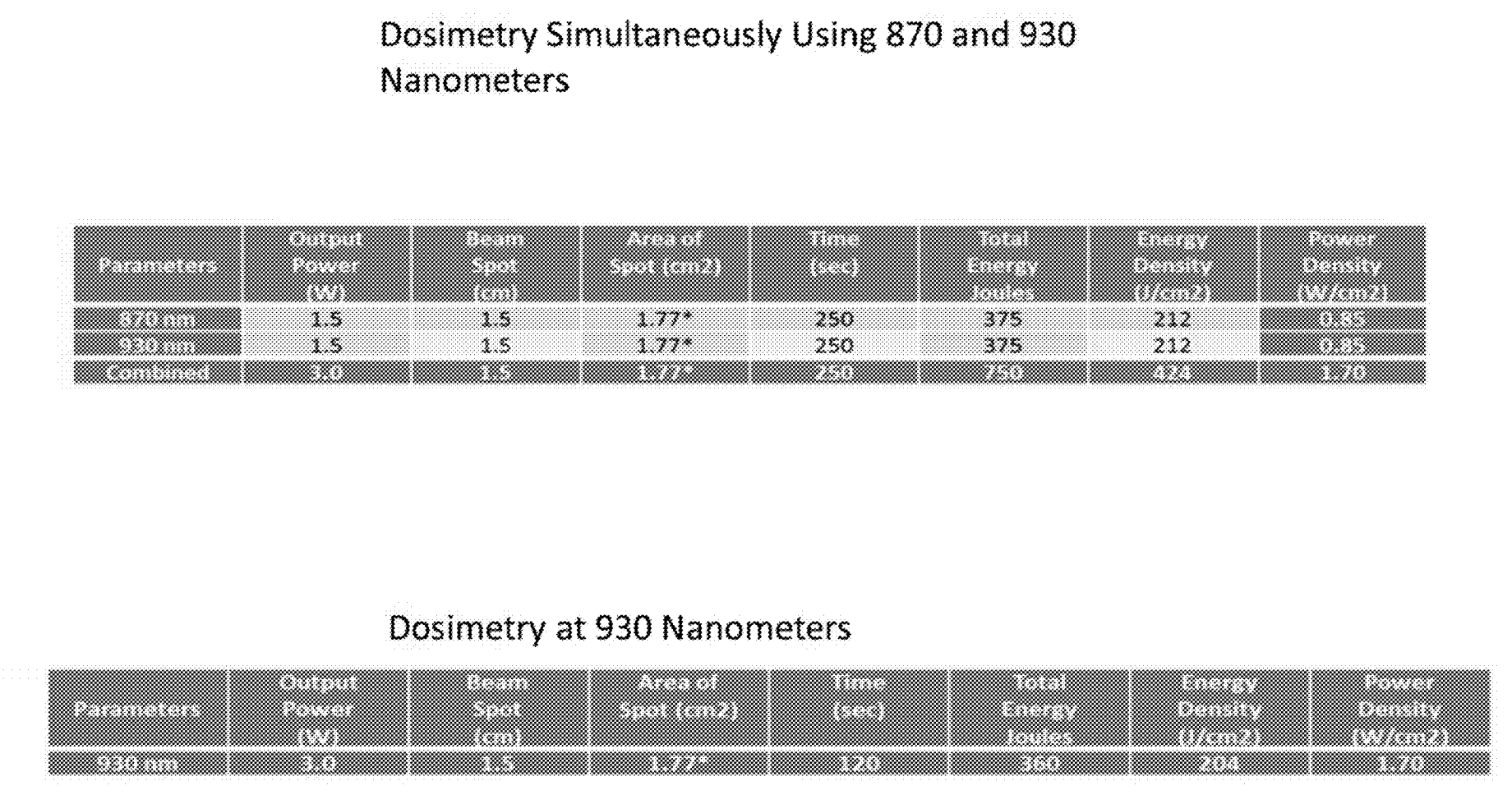

This inventor has established a photo-biologic Minimum Biofilm Inhibitory Concentration (PMBIC) with the NIMELS technology, with relation to biofilm producing strains of MRSA that were challenged with Ciprofloxacin. This inventor tested the effect in vivo against MRSA with the oral drug doxycycline. It was found that the sub-lethal "light doses" of the NIMELS technology (as summarized in FIG. 13) did in fact inhibit biofilm production in this MRSA patient, previously challenged with ciprofloxacin, and cured her with PMBIC and oral doxycycline (as shown in FIG. 12).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While the above detailed description has shown, described and identified several novel features of the invention as applied to a preferred embodiment, it will be understood that various omissions, substitutions and changes in the form and details of the described embodiments may be made by those skilled in the art without departing from the spirit of the invention. Accordingly, the scope of the invention should not be limited to the foregoing discussion, but should be defined by the appended claims.

What is claimed is:

1. A method for inhibiting biofilm production in Methicillin-resistant *Staphylococcus aureus* (MRSA) colonies in a human nasal cavity, the method comprising:
    applying, through a diffuser tip configured to generate a uniform cylindrical energy projection, treatment light to a treatment site in the nasal cavity in a manner configured to reduce a mutant prevention concentration for biofilm-producing MRSA in which:
        the treatment light comprises light with a first wavelength of about 870 nm and a second wavelength of about 930 nm;
        the treatment light is applied at a dosimetry comprising a power density of about 0.5 W/cm$^2$ to 0.75 W/cm$^2$ and an energy density of about 200 J/cm$^2$ to 400 J/cm$^2$ for a duration of about 300 seconds to 500 seconds per nostril; and
        the applied treatment light has a flat-top energy profile and is delivered in a continuous wave over the duration of application; and
    applying a Mupirocin formulation to the treatment site after or concurrently with applying the treatment light such that a concentration of Mupirocin that reaches the treatment site is greater than the mutant prevention concentration for biofilm-producing MRSA.

2. A method for inhibiting biofilm production in Methicillin-resistant *Staphylococcus aureus* (MRSA) colonies in a diabetic foot wound of a subject, the method comprising:
    applying, through an optical radiation delivery assembly configured to generate a uniform energy projection, treatment light to a treatment site in the diabetic foot wound in a manner configured to reduce a mutant prevention concentration for biofilm-producing MRSA in which:
        the treatment light comprises light with a first wavelength of about 870 nm and a second wavelength of about 930 nm;
        the treatment light is applied to the foot wound at a dosimetry comprising a power density of about 0.5 W/cm$^2$ to 0.75 W/cm$^2$ and an energy density of about 200 J/cm$^2$ to 400 J/cm$^2$ for a duration of about 300 seconds to 500 seconds; and the applied treatment light has a flat-top energy profile and is delivered in a continuous wave over the duration of application; and administering a Doxycycline formulation to the subject after or concurrently with applying the treatment light such that a concentration of Doxycycline that reaches the treatment site is greater than the mutant prevention concentration for biofilm-producing MRSA.

3. A method for preventing phenotypic upregulation of biofilm formation in Methicillin-resistant *Staphylococcus aureus* (MRSA) in a human nasal cavity during decolonization therapy, the method comprising:

applying, through a diffuser tip configured to generate a uniform cylindrical energy projection, treatment light to a treatment site in the nasal cavity in a manner configured to reduce a mutant prevention concentration for biofilm-producing MRSA in which:

the treatment light comprises light with a first wavelength of about 870 nm and a second wavelength of about 930 nm;

the treatment light is applied at a dosimetry comprising a power density of about 0.5 $W/cm^2$ to 0.75 $W/cm^2$ and an energy density of about 200 $J/cm^2$ to 400 $J/cm^2$ for a duration of about 300 seconds to 500 seconds per nostril; and the applied treatment light has a flat-top energy profile and is delivered in a continuous wave over the duration of application; and applying a topical Mupirocin formulation to the treatment site after or concurrently with applying the treatment light such that a concentration of Mupirocin that reaches the treatment site is greater than the mutant prevention concentration for biofilm-producing MRSA.

4. A method for preventing phenotypic upregulation of biofilm formation in Methicillin-resistant *Staphylococcus aureus* (MRSA) in a diabetic foot wound during decolonization therapy, the method comprising:

applying, through an optical radiation delivery assembly configured to generate a uniform energy projection, treatment light to a treatment site in the diabetic foot wound in a manner configured to reduce a mutant prevention concentration for biofilm-producing MRSA in which:

the treatment light comprises light with a first wavelength of about 870 nm and a second wavelength of about 930 nm;

the treatment light is applied to the foot wound at a dosimetry comprising a power density of about 0.5 $W/cm^2$ to 0.75 $W/cm^2$ and an energy density of about 200 $J/cm^2$ to 400 $J/cm^2$ for a duration of about 300 seconds to 500 seconds; and the applied treatment light has a flat-top energy profile and is delivered in a continuous wave over the duration of application; and applying a Doxycycline formulation to the application region after or concurrently with applying the treatment light such that a concentration of Doxycycline that reaches the treatment site is greater than the mutant prevention concentration for biofilm-producing MRSA.

* * * * *